United States Patent [19]

Dow et al.

[11] Patent Number: 5,351,692
[45] Date of Patent: Oct. 4, 1994

[54] LAPAROSCOPIC ULTRASONIC PROBE

[75] Inventors: Julian Dow, San Clemente; Paul F. Meyers, San Juan Capistrano; Michael Waddell, San Clemente, all of Calif.

[73] Assignee: Capistrano Labs Inc., San Clemente, Calif.

[21] Appl. No.: 75,121

[22] Filed: Jun. 9, 1993

[51] Int. Cl.$^5$ .................................. A61B 8/12
[52] U.S. Cl. .................. 128/662.06; 128/660.10; 128/660.09; 128/662.03
[58] Field of Search ............ 128/660.09, 660.10, 128/662.03, 662.06

[56] References Cited

U.S. PATENT DOCUMENTS

| | | | |
|---|---|---|---|
| 3,955,561 | 5/1976 | Eggleton | 128/2.05 Z |
| 4,092,867 | 6/1978 | Matzuk | 73/609 |
| 4,106,346 | 8/1978 | Matzuk | 73/614 |
| 4,149,419 | 4/1979 | Connell, Jr. et al. | 73/621 |
| 4,246,792 | 1/1981 | Matzuk | 73/620 |
| 4,271,706 | 6/1981 | Ledley | 73/614 |
| 4,282,879 | 8/1981 | Kunii et al. | 128/660 |
| 4,375,818 | 3/1983 | Suwaki et al. | 128/660 |
| 4,391,282 | 7/1983 | Ando et al. | 128/660 |
| 4,398,425 | 8/1983 | Matzuk | 73/633 |
| 4,399,703 | 8/1983 | Matzuk | 73/621 |
| 4,401,123 | 8/1983 | Baba | 128/660 |
| 4,421,118 | 12/1983 | Dow et al. | 128/660 |
| 4,424,813 | 1/1984 | Havlice et al. | 128/660 |
| 4,466,443 | 8/1984 | Utsugi | 128/660 |
| 4,479,388 | 10/1984 | Matzuk | 73/634 |
| 4,483,326 | 11/1984 | Yamaka et al. | 128/4 |
| 4,545,117 | 10/1985 | Okamoto | 29/596 |
| 4,584,880 | 4/1986 | Matzuk | 73/609 |
| 4,646,722 | 3/1987 | Silverstein et al. | 128/4 |
| 4,674,515 | 6/1987 | Andou et al. | 128/660 |
| 4,675,563 | 6/1987 | Goldowsky | 310/15 |
| 4,722,345 | 2/1988 | Ueno et al. | 128/660 |
| 4,756,313 | 7/1988 | Terwilliger | 128/660 |
| 4,785,819 | 11/1988 | Pearce | 128/660.10 |
| 4,831,292 | 5/1989 | Berry | 310/15 |
| 4,841,979 | 6/1989 | Dow et al. | 128/660.10 |
| 4,913,155 | 4/1990 | Dow et al. | 128/660.1 |
| 4,930,515 | 6/1990 | Tewilliger | 128/662.06 |
| 5,012,147 | 4/1991 | Bertram et al. | 310/80 |
| 5,048,529 | 9/1991 | Blumenthal | 128/660.1 |
| 5,085,221 | 2/1992 | Ingebrigtsen et al. | 128/660.1 |
| 5,111,092 | 5/1992 | Reinicke | 310/68 B |

*Primary Examiner*—George Manuel
*Attorney, Agent, or Firm*—Stetina and Brunda

[57] ABSTRACT

An ultrasonic probe has an elongate tubular member and an imaging ultrasonic transducer pivotally mounted proximate the distal end of the tubular member. Reciprocating pivotal motion of the ultrasonic transducer is effected to facilitate scanning. A first cable attached to the imaging ultrasonic transducer effects pivoting thereof in a first direction and a second cable attached to the imaging ultrasonic transducer effects pivoting thereof in a second direction. A linear motor is attached to the first cable for pulling the first cable to effect pivoting of the ultrasonic transducer in the first direction and a tension means is attached to the second cable for pulling the second cable when the linear motor ceases pulling the first cable to effect pivoting of the ultrasonic transducer in the second direction.

23 Claims, 4 Drawing Sheets

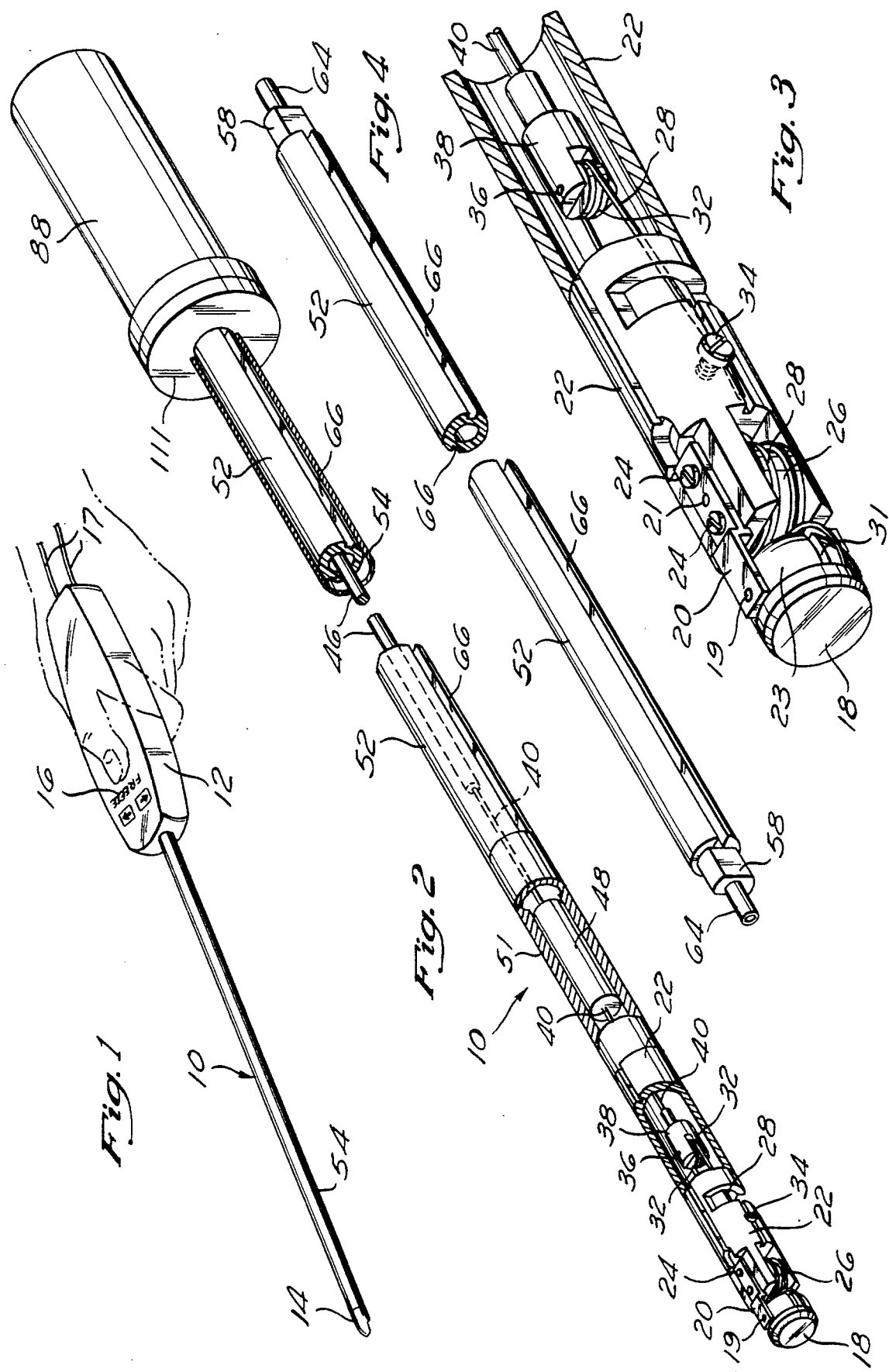

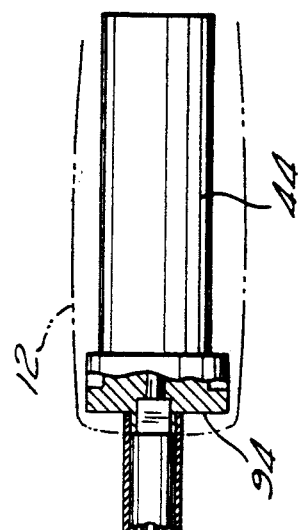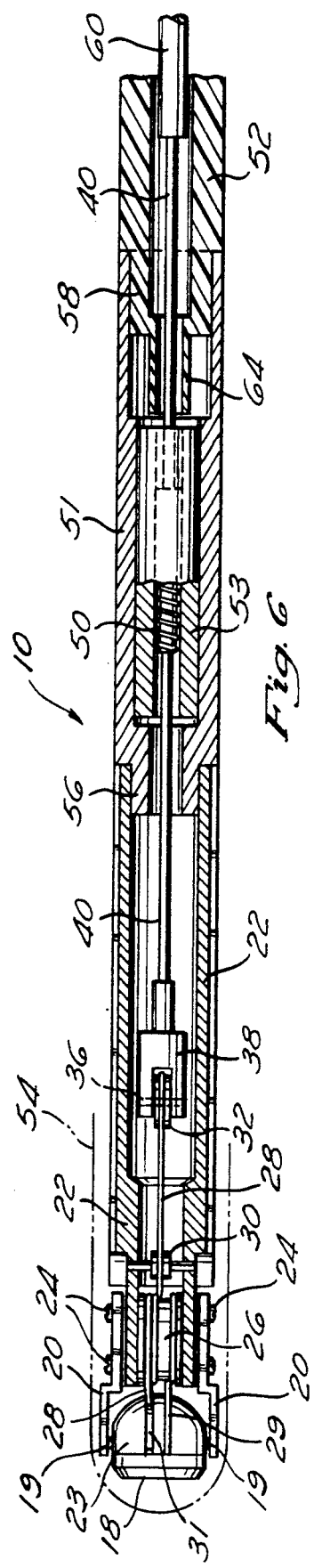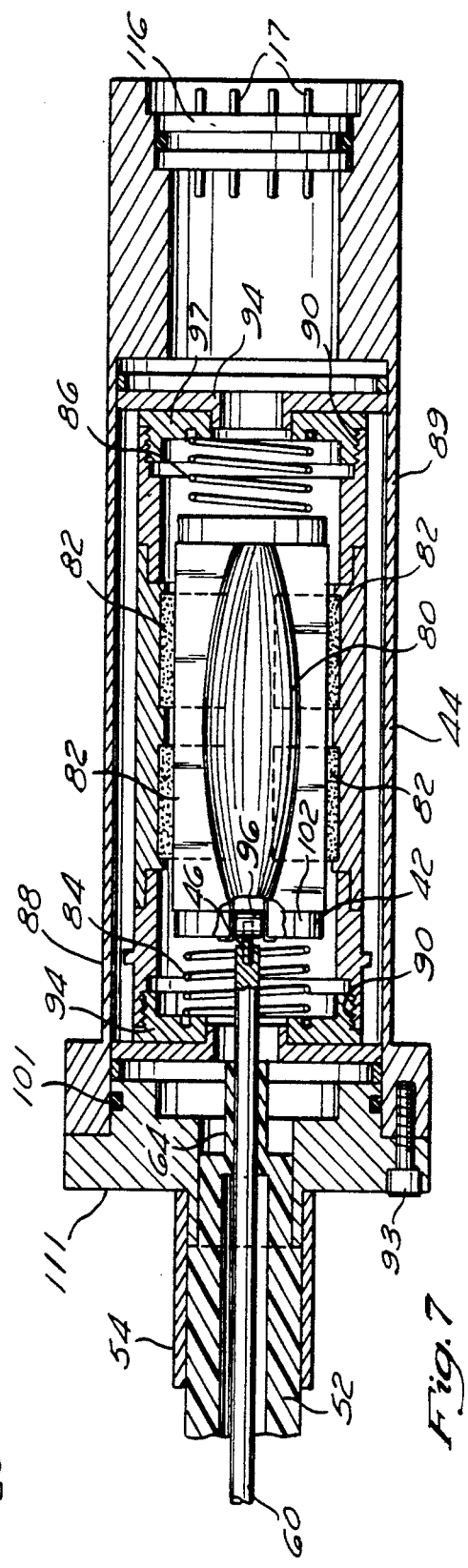

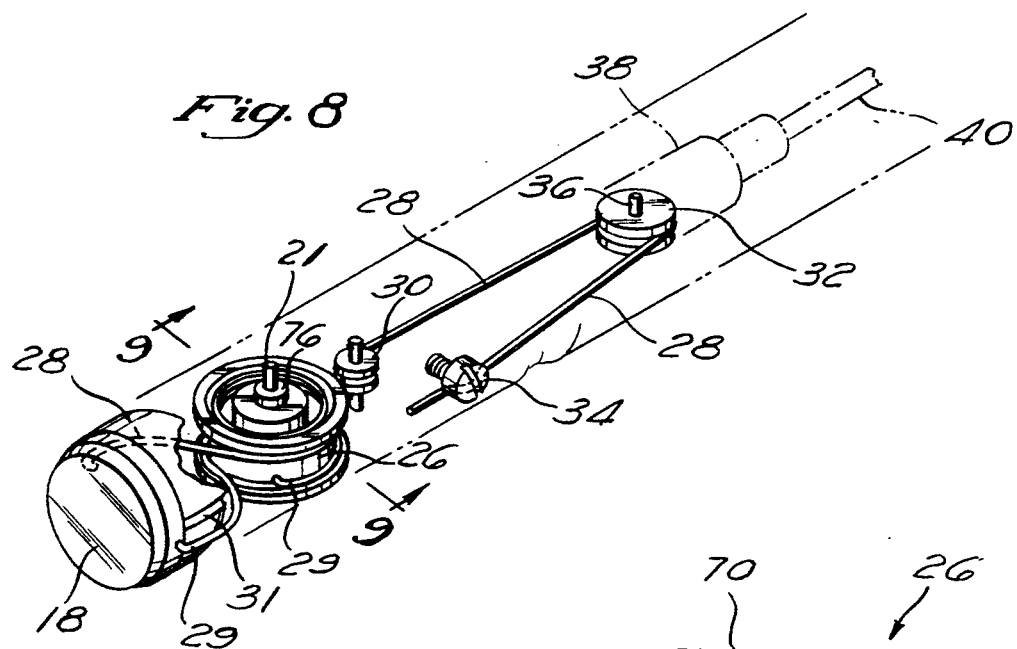
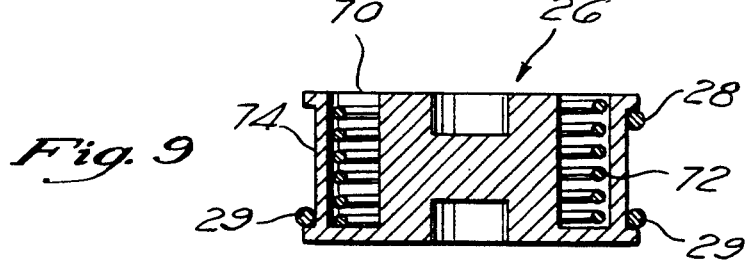
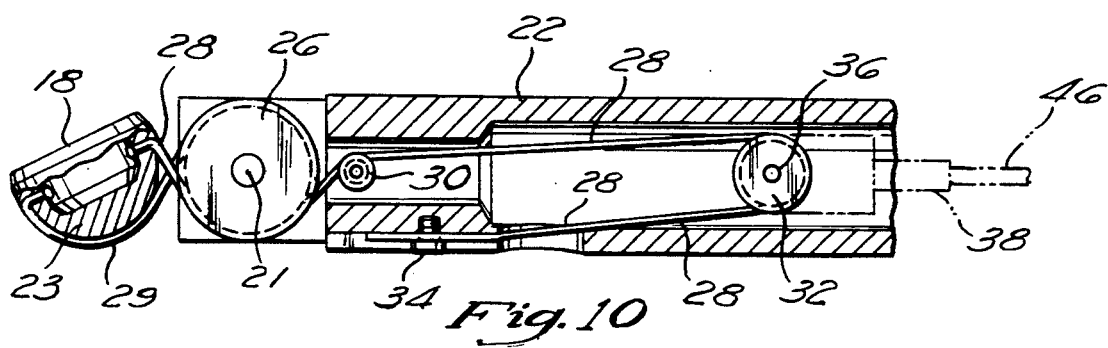
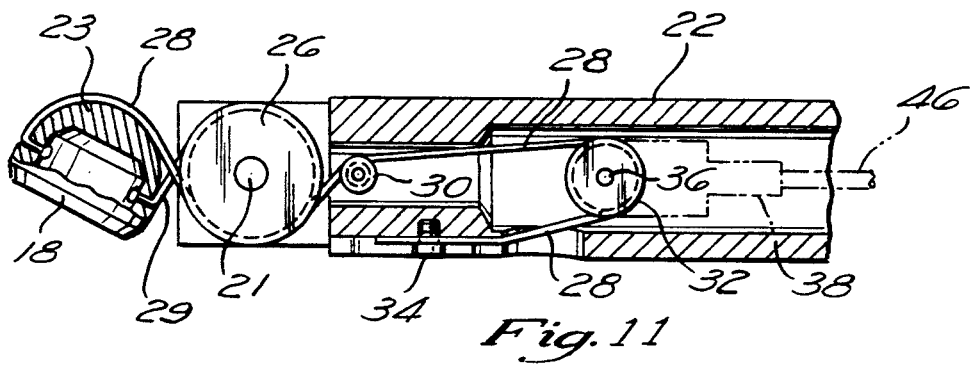

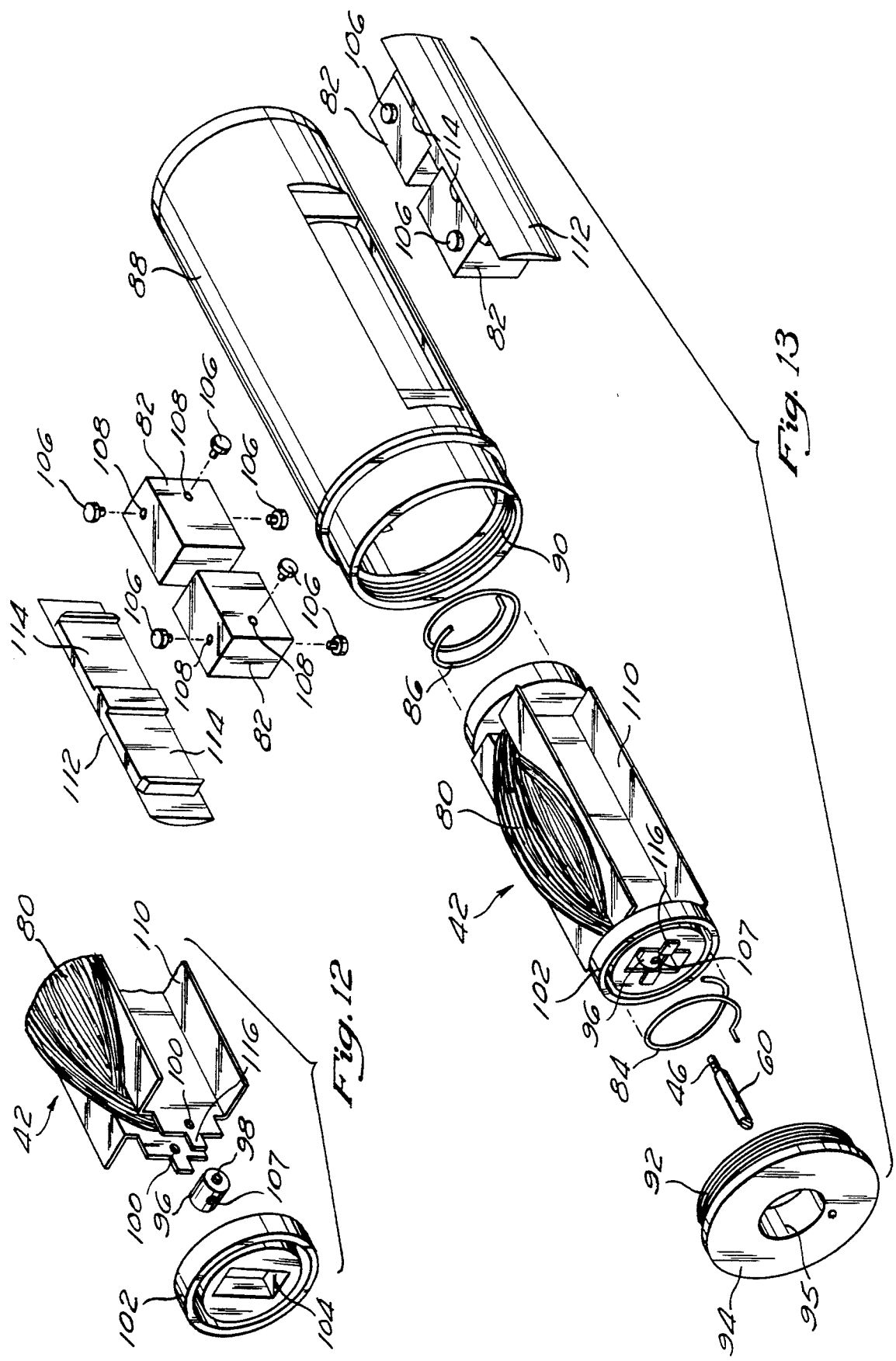

LAPAROSCOPIC ULTRASONIC PROBE

FIELD OF THE INVENTION

The present invention relates generally to ultrasonic probe assemblies for use in real-time diagnostic imaging and relates more specifically to a laparoscopic ultrasonic probe assembly for real-time imaging of internal anatomical structures such as the ovaries, uterus, and prostrate gland.

BACKGROUND OF THE INVENTION

In the field of ultrasonic diagnostics, acoustic images of anatomical structures are utilized in the diagnosis of various disorders. In order to produce real-time images of the anatomical structures, beams of ultrasonic energy from a probe are transmitted into the body tissue of a patient and echoes received by the ultrasonic probe are rapidly processed into an image format suitable for display. It is desirable that the probe produce an image over a wide field of view using a sector scan format. A sector scan format generates an image by repeatedly transmitting and receiving ultrasonic energy in radial directions away from the probe to define a fan-like pattern. The ultrasonic beam is directed by mechanically moving an ultrasonic transducer such that it is swept through an arc about a pivot axis to produce the fan-like sector scan pattern.

The prior art is replete with examples of ultrasonic transducer probe assemblies, such as those disclosed in U.S. Pat. No. 4,149,419 entitled "Ultrasonic Transducer Probe" issued Apr. 17, 1979 to R. Connell et al.; U.S. Pat No. 3,955,561 entitled "Cardioscan Probe" issued May 17, 1976 to R. Eggleton; U.S. Pat. No. 4,421,118 entitled "Ultrasonic Transducer" issued Dec. 20, 1983 to J. Dow et al.; U.S. Pat No. 4,479,388 entitled "Ultrasonic Transducer and Drive System" issued on Oct. 30, 1984 to T. Matzuk; U.S. Pat. No. 4,399,703 entitled "Ultrasonic Transducer and Integral Drive Circuit Therefor" issued on Aug. 23, 1983 to T. Matzuk; U.S. Pat No. 4,092,867 entitled "Ultrasonic Scanning Apparatus" issued on Jun. 6, 1978 to T. Matzuk; U.S. Pat. No. 4,246,792 entitled "Self-Contained Ultrasonic Scanner" issued Jan. 27, 1981 to T. Matzuk; U.S. Pat. No. 4,398,425 entitled "Ultrasonic Scanning Transducer" issued on Aug. 16, 1983 to T. Matzuk; U.S. Pat No. 4,841,979 entitled "Ultrasonic Prostate Probe Assembly" issued on Jun. 27, 1989 to Dow et al.; and U.S. Pat. No. 4,913,155 entitled "Ultrasonic Transducer Probe Assembly") issued On Apr. 3, 1990 to Dow et al.

Although all of the above-referenced patent disclosures address various problems associated with the use of ultrasonic transducer imaging, none have addressed the particular problems associated with the ultrasonic imaging of internal organs by positioning the ultrasonic probe within the body in close proximity to the organ to be imaged. More particularly, none of the cited patent disclosures address the problem of feeding an ultrasonic probe through narrow anatomical passageways such as the urethra, cervix, fallopian tubes, and major vessels of the vascular system, and the like.

Contemporary ultrasonic probe assemblies thus must image such internal anatomical structures through or around various obstructing anatomical structures, i.e. bones, blood vessels, and various organs. As such, the ability to image desired internal organs is often limited. The field of view may be severely restricted and/or the resolution reduced. Thus, it would be desirable to place an ultrasonic probe in close proximity to the organ being imaged even when that organ is disposed deep within surrounding tissue.

It is well known to provide visual images of internal organs by utilizing endoscopes. Various different types of endoscopes are known for viewing various anatomical structures. For example, upper endoscopes are utilized in the examination of the esophagus, stomach, and duodenum; colonoscopes are utilized for examining the colon, angioscopes are utilized for examining blood vessels, and arthroscopes are utilized for examining the various joint spaces. However, all such endoscopes are limited to providing visual images of the exterior surfaces or accessible portions of the desired anatomical structures. One cannot probe or see into the interior of organs when utilizing an endoscope without first disposing the endoscope within the organ. Thus, an invasive surgical procedure is necessary to utilize an endoscope in the viewing of such organs.

As such, although the prior art has recognized to a limited extent the problem of ultrasonically imaging internal or obstructed portions of the human anatomy, the proposed solutions have to date been ineffective in providing a satisfactory remedy.

SUMMARY OF THE INVENTION

The present invention specifically addresses and alleviates the above-mentioned deficiencies associated with the prior art. More particularly, the present invention comprises an elongate tubular member having proximal and distal ends and having a handle containing a linear motor at its proximal end and an imaging ultrasonic transducer pivotally mounted at the distal end of the tubular member. Means for effecting reciprocating pivotal motion of the imaging transducer preferably comprise at least one control cable extending through the tubular member and attached to the imaging ultrasonic transducer.

Preferably, a first cable having proximal and distal ends is attached at its distal end to the imaging ultrasonic transducer so as to effect pivoting of the imaging ultrasonic transducer in a first direction when the first cable is pulled and a second cable having proximal and distal ends is similarly attached at its distal end to the imaging ultrasonic transducer so as to effect pivoting of the imaging ultrasonic transducer in a second direction when the second cable is pulled.

The linear motor is attached to the proximal end of the first cable for pulling the first cable to effect pivoting of the imaging ultrasonic transducer in the first direction. A tension means, i.e. a spring, resilient member, electromagnetic means, etc., is attached to the proximal end of the second cable for pulling the second cable when the linear motor ceases pulling the first cable to effect pivoting of the imaging ultrasonic transducer in the second direction.

The elongate tubular member is preferably approximately 6 mm or less in diameter such that it may be inserted into various cavities, organs, vessels, and/or passageways of the body. For example, the elongate tubular member of the laparoscopic ultrasonic probe of the present invention can be passed through the urethra to facilitate ultrasonic imaging of the prostate gland. It can also be passed through the cervix to facilitate ultrasonic imaging of the uterus and passed through the fallopian tubes to facilitate ultrasonic imaging of the ovaries. Those skilled in the art will recognize that the laparoscopic ultrasonic probe of the present invention may be utilized in a wide variety of diagnostic and therapeutic treatments, particularly those wherein the anatomical structure to be imaged cannot be easily or clearly imaged by contemporary ultrasonic imaging devices.

The first and second cables are attached to the imaging ultrasonic transducer by wrapping them around the imaging ultrasonic transducer or at least a portion of the periphery thereof in order to minimize strain upon each of the first and second cables during reciprocating pivotal motion of the ultrasonic transducer. Thus, as each of the first and second cables is pulled in turn, the pulled cable unwinds from the imaging ultrasonic transducer, thus distributing the bending of the cable over a length thereof, rather than localizing the bending of the pulled cable at the point of attachment, as would be the case if direct, non-wrapping, attachment were utilized.

The proximal end of the first cable loops around a drive pulley mechanically attached to the linear motor such that the drive pulley reciprocates therewith and is then anchored to the tubular member, preferably in a manner such that the length thereof is variable. The proximal end of the second cable wraps around a spring-biased spool and is anchored thereto such that rotation of the spring-biased spool in a direction which pulls the second cable results in pivotal movement of the transducer member in a second direction.

In the preferred embodiment of the present invention, the distal end of the first cable is anchored to the transducer member such that pulling the first cable results in pivotal movement of the transducer member in a first direction. The first cable wraps around the spring-biased spool, preferably for approximately one complete turn, and then passes over a centering pulley which positions the first cable such that it then travels longitudinally in a proximal direction to the drive pulley. The first cable loops around the drive pulley and then extends distally to an adjustment screw which serves as an anchoring point therefore. By turning the adjustment screw to which the proximal end of the first cable is attached, the length of the first cable is adjusted so as to adjust the rest position of the transducer member.

The drive pulley is mechanically linked to the linear motor, preferably via a rigid member, such that linear movement of the linear motor armature results in like linear movement of the drive pulley. Thus, retraction of the linear motor armature into the linear motor results in proximal movement of the drive pulley, thereby pulling the first cable so as to effect movement of the imaging transducer member in the first direction. Conversely, extension of the linear motor armature from the linear motor results in distal movement of the drive pulley, thereby allowing the spring-biased spool to pull the second cable so as to effect movement of the imaging transducer in the second direction.

The second cable loops about the spring-biased spool, preferably for approximately one complete turn. The spring-biased spool utilizes a spring member, preferably a coil spring, disposed therein, to apply tension to the second cable so as to apply tension to the second cable and thereby pivotally move the transducer member in the second direction when tension is released from the first cable.

A position sensor, preferably a linear variable differential transformer (LVDT) is formed about the rigid drive member intermediate the drive pulley and the linear motor so as to provide an indication of the position of the transducer member during operation thereof. Those skilled in the art will recognize that various other positionsensing means are likewise suitable. The core of the LVDT is thus integrated into the drive mechanism of the laparoscopic ultrasonic probe of the present invention and thus moves therewith.

As is well known to those skilled in the art, the LVDT produces an electrical output proportional to the displacement of the core. Alternating current carrier excitation is applied to the primary coil of the LVDT. Two identical secondary coils are symmetrically spaced relative to the primary coil and are connected externally in a series-opposing circuit. Changing the position of the core relative to the remainder of the transformer varies the mutual inductance of each secondary coil relative to the primary coil, which thus determines the voltage induced from the primary coil to each secondary coil. If the core is centered between the secondary coils, the voltage in each secondary coil is identical and 180 degrees out of phase. Thus, in this situation there is no net output voltage.

Using the position output signal of the LVDT, a smaller segment of the imaging ultrasonic transducer member's movement can be controlled by setting unique reference voltages in which the position signal can be compared to the reference voltages. The probe can thus be caused to oscillate between two positions as indicated by these reference voltages. Thus, a variable scan direction and/or angle is facilitated. Continuously variable angles can be achieved by introducing a DC offset voltage to the position signal, thereby allowing a smaller scan angle to be rotated to any position within the larger scan angle. That is, a smaller viewing window can be defined within the maximum scan angle limits.

The scan angle can be controlled using control signals generated from switches in the probe handle. The control signals will vary the position reference voltages and/or position of set voltages, thereby enabling the selection of scan direction from the probe by the user.

Electrical conduits for providing control, data, and/or power to the imaging ultrasonic transducer are provided by the pivot mount brackets attached thereto.

Thus, the position sensor provides a signal representative of the angle at which the imaging ultrasonic transducer is disposed. Those skilled in the art will recognize the need for such position information utilized in the ultrasonic imaging process.

The position sensor alternatively comprises a metal member, preferably ferrous, disposed upon either the first cable, the second cable, or the elongate rigid member, and having a coil formed thereabout such that motion of the cable, corresponding to motion of the imaging ultrasonic transducer, results in movement of the metal member into and out of the coil. Thus, the inductance of the coil varies with position of the imaging ultrasonic transducer and is representative thereof.

In the operation of the preferred embodiment of the present invention, the linear motor is actuated to move the armature thereof proximally and thus to move the drive pulley proximally such that the first cable, passing thereover and anchored to the elongate tubular member is pulled and thereby effects pivotal movement of the imaging ultrasonic transducer to which the distal end of the cable is attached in a first direction. Extension of the armature of the linear motor removes tensions from the first cable and thereby allows the tension means or spring-biased spool to effect movement of the imaging ultrasonic transducer in a second direction opposite that of the first direction. The spring-biased spool pulls the second cable passing thereover and anchored thereto so as to effect movement of the imaging ultrasonic transducer in the second direction. Thus, alternating linear motion of the linear motor results in reciprocating pivotal motion of the imaging ultrasonic transducers.

Thus, the tension means or spring-biased spool accommodates motion of the second cable when the linear motor effects movement of the imaging ultrasonic transducer in the first direction and the tension means causes movement of the second cable when the linear motor ceases effecting movement of the imaging ultrasonic transducer in the first direction. As such, the resilient means acts as a spring or restorative force for biasing the imaging ultrasonic transducer in the second direction.

As the imaging ultrasonic transducer moves in the first direction, the first cable unwinds from the periphery thereof and the second cable winds onto the periphery thereof, thus minimizing bending strain at the distal end of the first and second cables. As the imaging ultrasonic transducer moves in the second direction, this process is reversed.

Movement of the rigid elongate member attached intermediate the armature of the linear motor and the drive pulley effects like movement of the LVDT core attached thereto relative to the stationary coils of the LVDT attached to the elongate tubular member. Thus, a signal representative of the position of the transducer member is provided. Those skilled in the art will recognize that various other configurations of the position sensor are likewise suitable.

A doppler ultrasonic transducer may optionally be provided at the distal end of the elongate tube, formed upon or proximate the imaging ultrasonic transducer. The doppler ultrasonic transducer would thus provide flow information, i.e. blood flow through a portion of the vascular system.

These, as well as other, advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1 is a perspective view of the laparoscopic ultrasonic probe of the present invention;

FIG. 2 is an enlarged perspective view of the laparoscopic ultrasonic probe of FIG. 1, partially in section;

FIG. 3 is an enlarged sectional view of the distal end of the laparoscopic ultrasonic probe;

FIG. 4 is an enlarged fragmentary view of the elongate tubular member;

FIG. 5 is a cross-sectional view of the laparoscopic ultrasonic probe of the present invention;

FIG. 6 is an enlarged cross-sectional view of the distal end of the laparoscopic ultrasonic probe;

FIG. 7 is an enlarged cross-sectional view of the proximal end of the laparoscopic ultrasonic probe of the present invention, showing the linear drive motor thereof;

FIG. 8 is an enlarged perspective view of the functional components disposed at the distal end of the laparoscopic ultrasonic probe of the present invention;

FIG. 9 is an enlarged cross-sectional view of the spring-biased spool, showing the coil spring disposed therein;

FIG. 10 is an enlarged cross-sectional view of the functional components of FIG. 8 showing the transducer member disposed in a first position;

FIG. 11 is an enlarged cross-sectional view of the functional components of FIG. 8 showing the transducer member disposed in a second position;

FIG. 12 is an exploded perspective view of the distal end of the armature of the linear motor; and FIG. 13 is an exploded view of the linear motor.

DETAILED DESCRIPTION OF THE PREFERRED EMBODIMENT

The detailed description set forth below in connection with the appended drawings is intended as a description of the presently preferred embodiment of the invention, it is not intended to represent the only form in which the present invention may be constructed or utilized. The description sets forth the functions and sequence of steps for constructing and operating the invention in connection with the illustrated embodiment. It is to be understood, however, that the same or equivalent functions or sequences may be accomplished by different embodiments that are also intended to be encompassed within the spirit and scope of the invention.

The laparoscopic ultrasonic probe of the present invention is illustrated in FIGS. 1-13 which depict a presently preferred embodiment of the invention. Referring now to FIG. 1, the laparoscopic ultrasonic probe is comprised generally of an elongate probe 10 and a handle 12. A window 14 is disposed at the distal end of the elongate probe 10. Controls 16 formed upon the handle 12 facilitate changing of the view angle or window and/or freezing of the scanned image. Power and signal cables 17 facilitate electrical communication between the laparoscopic ultrasonic probe of the present invention and its associated electronics.

Referring now to FIGS. 2-9, an imaging ultrasonic transducer 18 is disposed at the distal end of the probe 10 and is mounted upon gimbal brackets 20 via pivot pin 19. The gimbal brackets 20 attach to distal housing 22, preferably via screws 24.

A doppler ultrasonic transducer may optionally be positioned proximate the imaging ultrasonic transducer so as to provide information regarding the flow of fluids through various anatomical vessels.

A spring-biased spool 26 is rotatably mounted within the distal housing 22. A first cable 28 extends proximally from the imaging ultrasonic transducer 18, wraps around the spring-biased spool 26, preferably for approximately one full turn, and then extends proximally to centering pulley 30 (best shown in FIGS. 6, 8, 10, and 11). The centering pulley 30 aligns the first cable 28 such that it extends proximally approximately parallel to the longitudinal axis of the probe 10. The first cable 28 extends to and loops around the drive pulley 32 and then extends distally to adjustment screw 34 to which it is anchored, preferably through a hole formed therein, such that rotation of adjustment screw 34 varies the length of the first cable 28 so as to adjust the rest or centered position of the imaging ultrasonic transducer 18.

The drive pulley 32 is pivotally mounted, via pin 36, to drive pulley housing 38. The drive pulley housing 38 is rigidly attached to rigid elongate drive member 40 which extends proximally through elongate tubular member 52 and is attached rigidly to the armature 42 of linear motor 44, preferably via threaded stud 46. The proximal end portion of the rigid elongate drive member 40 is formed to comprise a thicker portion, i.e. region of increased diameter, 40 so as to increase the rigidity thereof. Threaded member 46 is received in the proximal end of the rigid elongate drive member 40 and connects the rigid elongate drive member 40 to the armature 42.

The second cable 29 extends proximally from the imaging ultrasonic transducer 18 to the spring-biased spool 26 and wraps thereabout, preferably for approximately one turn, in a direction opposite that of the first cable 28. Attachment of the first 28 and second 29 cables to the imaging ultrasonic transducer 18 is done at diametrically opposed positions thereof such that pulling the first cable 28 results in rotation of the imaging ultrasonic transducer 18 in a first direction and pulling the second cable 29 results in rotation of the imaging ultrasonic transducer 18 in a second direction.

With particular reference to FIG. 9, the spring-biased spool 26 is attached to the distal housing 22 via pivot pin 21 and comprises a channel 70 within which a coil spring 72 is disposed. A groove 74 is formed about the outer periphery of the spring-biased spool 26 and receives the first 28 and second 29 cables. One end of the coil spring 72 is attached to the spring-biased spool 26 and the opposite end thereof is attached to the spindle 76 about which the spring-biased spool 26 rotates such that the coil spring 72 applies tension to the second cable 29. That is, the coil spring 72 is partially wound or preloaded within the spring-biased spool 26 such that a predetermined amount of tension is applied to the imaging ultrasonic transducer 18 so as to urge the imaging ultrasonic transducer 18 in the second direction.

A position sensor, preferably a linear variable differential transformer (LVDT) 48, senses the position of the imaging ultrasonic transducer 18 by sensing the position of the rigid elongate drive member 40, the position of which varies proportionally to the position of the imaging ultrasonic transducer 18. The LVDT 48 comprises a core coil 50 (as shown in FIG. 6) attached to the rigid elongate member 40 and at least one surrounding coil 53 attached to the elongate tubular member 52.

The distal housing 22 attaches to a position sensor housing 51 within which the position sensor or LVDT 48 is disposed. Position sensor housing 51 attaches to elongate tubular member 52 through which the rigid elongate drive member 40 extends. The elongate tubular member 52 extends from the position sensor housing 51 to the handle 12 and attaches to the linear motor 44 disposed therein.

Sleeve 54 surrounds the distal housing 22, position sensor housing 51, and elongate tubular member 52 and thus forms the outer surface of the probe 10 except for the window 14. The window 14 is comprised of an ultrasonic transmissive material to facilitate imaging of anatomical structures by the imaging ultrasonic transducer 18.

The position sensor housing 51 has an area of reduced diameter 56 formed at the distal end thereof and received by the distal housing 22 to facilitate attachment thereto. In a similar manner the elongate tubular member 52 has a region of reduced diameter 58 formed at the distal end thereof and received by the position sensor housing 51 to facilitate attachment thereto.

With particular reference to FIG. 4, the tubular elongate member 52 comprises cylindrical guide members 64 formed upon the regions of reduced diameter 58 at both the proximal and distal ends thereof for maintaining desired positioning of the rigid elongate member 40 disposed longitudinally within the elongate tubular member 52. Grooves 66 formed along the length of the elongate tubular member 52 provide pathways for electrical conduits (not shown) extending the length of the probe 10 to facilitate operation of the imaging ultrasonic transducer 18. The electrical conduits preferably provide electrical contact to the imaging ultrasonic transducer 18 via the gimbal brackets 20. Those skilled in the art will recognize that the electrical conduits may optionally contact the imaging ultrasonic transducer 18 via the first 26 and second 27 cables.

Referring now to FIGS. 7, 12, and 13, the linear motor 44 is disposed within the handle 12 of the laparoscopic ultrasonic probe of the present invention and generally comprises an armature 42 about which armature coil 80 is wound. Four permanent magnets 82 are disposed about the armature 42 such that the application of an ultrasonic excitation voltage to the armature coil 80 results in ultrasonic linear reciprocation of the armature 42. First 84 and second 86 centering springs maintain a centered position of the armature 42 within the linear motor housing 88 when no excitation voltage is applied.

The linear motor housing 88 is a generally cylindrical, preferably stainless steel, enclosure having female threads 90 formed in both the proximal and distal ends thereof for receiving and threadably engaging complimentary male threads formed upon end caps 94. A cylindrical nut 96 having bosses 98 formed at opposite ends thereof is attached via the bosses 98 to the armature 42. The bosses 98 of the cylindrical nut 96 are received within complimentary apertures 100 formed upon the distal end of the armature 42. The armature 42 further comprises an end cap 102 having a slot 104 formed therein. Threaded aperture 107 of the cylindrical nut 96 receives the threaded stud 46 of the rigid elongate member 60.

Tabs 116 formed at the distal end of the armature 42 are bent over after being inserted through slot 10 formed in the end piece 102 of the armature 42 so as to attach the end piece 102 thereto.

Delron inserts 106 are received within complimentary apertures 108 formed within each magnet 82 so as to provide low-friction bearing surfaces along which the armature 42 reciprocates. Grooves 110 formed in the armature 42 receive the magnets 82 in such a manner that the armature 42 is free to reciprocate longitudinally within the housing 88 and is prevented from rotating. Magnet holders 112 secure the magnets 82 in place within the housing 88. Cutouts 114 formed within each magnet holder 112 receive the outboard surfaces of each magnet 82 so as to prevent longitudinal sliding of the magnets 82 as the armature 42 slides longitudinally thereover.

Those skilled in the art will recognize that various linear drive mechanisms are likewise suitable for effecting reciprocating motion of the elongate rigid member 46 of the present invention.

The rigid elongate member 60 is received through opening 95 formed in the end cap 94. A second end cap 97 is disposed in a similar manner at the proximal end of the housing 88.

The end cap 94 is further secure to the housing 88 via a fastener, such as screw 93, which is received within aperture 91 formed in the end cap 94 and thus prevents undesirable rotation of the end cap 94 relative to the body 88 and consequent loosening thereof. An O-ring 101 disposed about the end cap 94 prevents the leakage of fluid into the housing 88 where it may have detrimental effects upon the linear motor 44.

Conductive conduits 17 extend through strain-relief grommet 116 and out of the distal end of the handle 12.

Having thus described the structure of the laparoscopic ultrasonic probe of the present invention, it may be beneficial to describe the operation thereof. The application of an ultrasonic drive signal to the armature coil 80 of the linear motor 44 causes the armature to reciprocate longitudinally at an ultrasonic frequency. The elongate rigid member 40 attached to the armature 42 therefore likewise reciprocates at an ultrasonic frequency and causes the drive pulley 32 pivotally attached to the distal end of the elongate rigid member 40 to likewise reciprocate.

Reciprocation of the drive pulley 32 in the proximal direction pulls the first cable 28 causing the spring-biased spool 26 to rotate so as to continue to pull the first cable 28 and thereby increase tension upon the second cable 29. Pulling the first cable causes the ultrasonic transducer 18 to rotate in the first direction.

Reciprocation of the drive pulley 32 distally reduces tension upon the first cable 28 so as to allow the coil spring 72 of the spring-biased spool 26 to cause the spring-biased spool 26 to rotate so as to allow the second cable 29 to pull the ultrasonic transducer 18, thus causing the ultrasonic transducer 18 to rotate in the second direction.

Thus, the application of tension to the first cable 28 by the linear motor 44 through the elongate rigid member 40 effects movement of the ultrasonic transducer in the first direction and lessening of the tension applied by the first cable 28 allows the coil spring 72 to cause the ultrasonic transducer 18 to rotate in the second direction.

Tightening of the adjustment screw 34 shortens the length of the first cable 28 so as to move the ultrasonic transducer in the first direction and loosening of the adjustment screw 34 lengthens the first cable 28 so as to move the ultrasonic transducer in the second direction. Thus, the rest position and/or the end points or maximum limits of travel of the ultrasonic transducer 18 may be adjusted by turning the adjustment screw 34. That is, turning the adjustment screw 34 varies the position of the angle sweep by the imaging ultrasonic transducer 18.

Reciprocation of the elongate rigid member 40 results in like movement of the moving coil of the LVDT of the position sensor 48, and thus provides a signal indicative of the angular position of the imaging ultrasonic transducer 18.

Controls 16 disposed upon the handle 12 electronically control the application on the excitation voltage to the armature 42 of the linear motor 44 so as to control the movement of the ultrasonic transducer 18 and thus vary the ultrasonic image provided thereby. Thus, the sweeping motion of the ultrasonic transducer 18 may be limited to a portion of its travel or stopped entirely by varying the drive signal to the linear motor 44, thus controlling the angle of ultrasonic imaging. Thus, the imaging ultrasonic transducer 18 provides an image in any direction selected by the user. For example, a front view or a side view, as desired, may be selected by the user.

Alternatively, the ultrasonic transducer 18 may be permitted to travel throughout the entire angle of its range and various view windows, then be electronically imaged within that range. That is, although the ultrasonic transducer 18 travels the full range of its arc, an ultrasonic image may be provided only for a portion of that travel, as desired. Thus, the imaging ultrasonic transducer provides an image for a selected portion of its pre-set physical scan angle. The physical scan angle itself is also optionally selectable by the user.

Grooves 31 formed in the base 23 of the imaging ultrasonic transducer 18 facilitate wrapping of the first 28 and second 29 cables about the base 23 of the imaging ultrasonic transducer 18 so as to evenly distribute the strain experienced by each cable during the process of effecting reciprocating arcuate motion of the imaging ultrasonic transducer 18.

It is understood that the exemplary laparoscopic ultrasonic probe assembly of the present invention, described herein and shown in the drawings, represents only a present preferred embodiment of the invention. Indeed, various modifications and additions may be made to such embodiment without departing from the spirit and scope of the invention. For example, the control cable or cables may be configured in various manners, i.e. over various pulleys, etc., so as to effect reciprocating pivotal motion of the imaging ultrasonic transducer. Additionally, those skilled in the art will recognize that various different position sensing means and various different tension means are likewise suitable for use in the laparoscopic ultrasonic probe of the present invention. Thus, these and other modifications and additions may be obvious to those skilled in the art and may be implemented to adapt the present invention for use in a variety of different applications.

What is claimed is:

1. An ultrasonic probe comprising:
   (a) an elongate tubular member having proximal and distal ends;
   (b) an imaging ultrasonic transducer pivotally mounted proximate the distal end of said tubular member; and
   (c) cable means for effecting reciprocating pivotal motion of said imaging ultrasonic transducer, comprising:
      a first cable having proximal and distal ends, said first cable being attached at its distal end to said imaging ultrasonic transducer to effect pivoting of said imaging ultrasonic transducer in a first direction when said first cable is pulled;
      a second cable having proximal and distal ends, said second cable being attached at its distal end to said imaging ultrasonic transducer to effect pivoting of said imaging ultrasonic transducer in a second direction when said second cable is pulled;
      a linear motor attached to said first cable for pulling said first cable to effect pivoting of said imaging ultrasonic transducer in the first direction; and
      a tension means attached to said second cable for pulling said second cable when said linear motor ceases pulling said first cable to effect pivoting of said imaging ultrasonic transducer in the second direction.

2. The ultrasonic probe as recited in claim 1 wherein said tubular member is approximately 6 mm in diameter.

3. The ultrasonic probe as recited in claim 1 further comprising a doppler ultrasonic transducer disposed proximate said imaging ultrasonic transducer.

4. The ultrasonic probe as recited in claim 1 further comprising a position sensor for detecting the position of said imaging ultrasonic transducer.

5. The ultrasonic probe as recited in claim 4 wherein said position sensor comprises:
   a) a metal member attached to one of said first and second cables; and
   b) a coil through which said metal member moves as said imaging ultrasonic transducer reciprocates, the inductance of said coil varying with the position of said metal member therein.

6. The ultrasonic probe as recited in claim 4 wherein said position sensor comprises a linear voltage differential transformer.

7. The ultrasonic probe as recited in claim 1 wherein said first and second cables attach directly to said imaging ultrasonic transducer by wrapping around said imaging ultrasonic transducer to minimize strain upon said first and second cables during reciprocating pivotal motion of said ultrasonic transducer, 8. An ultrasonic probe comprising:
   (a) an elongate tubular member having proximal and distal ends;
   b) an imaging ultrasonic transducer pivotally mounted proximate the distal end of sad tubular member;
   c) means for effecting reciprocating pivotal motion of said imaging ultrasonic transducer; and
   d) a position sensor for detecting the position of said imaging ultrasonic transducer, said position sensor comprising:
      i) a metal member attached to one of said first and second cables; and
      ii) a coil through which said metal member moves as said imaging ultrasonic transducer reciprocates, the inductance of said coil varying with the position of said metal member therein.

9. The ultrasonic probe as recited in claim 8 wherein said tubular member is approximately 6 mm in diameter.

10. The ultrasonic probe as recited in claim 8 wherein said means for effecting reciprocating pivotal motion of said ultrasonic transducer comprises at least one control cable extending through said tubular member and attached to said imaging ultrasonic transducer.

11. The ultrasonic probe as recited in claim 8 wherein said means for effecting reciprocating pivotal motion of said imaging ultrasonic transducer comprises:
   a) a first cable having proximal and distal ends attached at its distal end to said imaging ultrasonic transducer to effect pivoting of said imaging ultrasonic transducer in a first direction when said first cable is pulled;
   b) a second cable having proximal and distal ends, attached at its distal end to said imaging ultrasonic transducer to effect pivoting of said imaging ultrasonic transducer in a second direction when said second cable is pulled;
   c) a linear motor attached to said first cable for pulling said first cable to effect pivoting of said imaging ultrasonic transducer in the first direction; and
   d) a tension means attached to said second cable, for pulling said second cable when said linear motor ceases pulling said first cable to effect pivoting of said imaging ultrasonic transducer in the second direction.

12. The ultrasonic probe as recited in claim 11 further comprising a doppler ultrasonic transducer disposed proximate said imaging ultrasonic transducer.

13. An ultrasonic probe comprising:
   a) an elongate tubular member having proximal and distal ends;
   b) an imaging ultrasonic transducer pivotally mounted proximate the distal end of said tubular member;
   c) means for effecting reciprocating pivotal motion of said imaging ultrasonic transducer; and
   d) a position sensor for detecting the position of said imaging ultrasonic transducer, said position sensor comprising a linear voltage differential transformer.

14. The ultrasonic probe as recited in claim 13 wherein said tubular member is approximately 6 mm in diameter.

15. The ultrasonic probe as recited in claim 13 wherein said means for effecting reciprocating pivotal motion of said ultrasonic transducer comprises at least one control cable extending through said tubular member and attached to said imaging ultrasonic transducer.

16. The ultrasonic probe as recited in claim 13 wherein said means for effecting reciprocating pivotal motion of said imaging ultrasonic transducer comprises:
   a) a first cable having proximal and distal ends, attached at its distal end to said imaging ultrasonic transducer to effect pivoting of said imaging ultrasonic transducer in a first direction when said first cable is pulled;
   b) a second cable having proximal and distal ends, attached at its distal end to said imaging ultrasonic transducer to effect pivoting of said imaging ultrasonic transducer in a second direction when said second cable is pulled;
   c) a linear motor attached to said first cable for pulling said first cable to effect pivoting of said imaging ultrasonic transducer in the first direction; and
   d) a tension means attached to said second cable for pulling said second cable when said linear motor ceases pulling said first cable to effect pivoting of said imaging ultrasonic transducer in the second direction.

17. The ultrasonic probe as recited in claim 16 further comprising a doppler ultrasonic transducer disposed proximate said imaging ultrasonic transducer.

18. An ultrasonic probe comprising:
   a) an elongate tubular member having proximal and distal ends;
   b) an imaging ultrasonic transducer pivotally mounted proximate the distal end of said tubular member; and
   c) a first cable having a distal end attached to said imaging ultrasonic transducer and a proximal end attached to a linear motor such that activation of said linear motor effects movement of said imaging ultrasonic transducer in a first direction and rotation of said spring-biased pulley in a first direction;
   d) a second cable having a distal end attached to said imaging ultrasonic transducer and a proximal end attached to a spring-biased pulley such that rotation of said spring-biased pulley in a second direction effects movement of said imaging ultrasonic transducer in a second direction opposite to said first direction; and e) wherein said linear motor comprises:
  i) a housing;
  ii) an armature slidably disposed within said housing;
  iii) a plurality of magnets disposed proximate said armature;
  iv) at least one magnet holder receiving the outboard surfaces of each magnet;
  v) bearing surfaces formed upon said magnets and slidable contacting said armature; and
  vi) wherein said magnets are captured intermediate said magnet holder(s) and said armature and are prevented from sliding longitudinally by said magnet holder.

19. The ultrasonic probe as recited in claim 18 wherein said imaging ultrasonic transducer provides an image in a direction selected by the user.

20. The ultrasonic probe as recited in claim 18 wherein said imaging ultrasonic transducer provides a front view or a side view, as selected by the user.

21. The ultrasonic probe as recited in claim 18 wherein said imaging ultrasonic transducer provides an image for a selected portion of its physical scan angle.

22. The ultrasonic probe as recited in claim 18 wherein the physical scan angle of said imaging ultrasonic transducer is selectable by the user.

23. An ultrasonic probe comprising:

an elongate tubular member having proximal and distal ends;

an imaging ultrasonic transducer pivotally mounted proximate the distal end of said tubular member;

a first cable having a distal end attached to said imaging ultrasonic transducer and a proximal end attached to a linear motor such that activation of said linear motor effects movement of said imaging ultrasonic transducer in a first direction and rotation of a spring-biased pulley in a first direction;

a second cable having a distal end attached to said imaging ultrasonic transducer and a proximal end attached to a spring-biased pulley such that rotation of said spring-biased pulley in a second direction effects movement of said imaging ultrasonic transducer in a second direction opposite to said first direction;

wherein said linear motor comprises a housing, an armature slidable disposed within said housing, a plurality of magnets disposed proximate said armature, at least one magnet holder receiving the outboard surfaces of each magnet, bearing surfaces formed upon said magnets and slidably contacting said armature; and wherein said magnets are captured intermediate said magnet holder and said armature and are prevented from sliding longitudinally by said magnet holder.

* * * * *